United States Patent
Zhang et al.

(10) Patent No.: US 9,433,709 B2
(45) Date of Patent: Sep. 6, 2016

(54) INTERVENTIONAL MEDICAL DEVICE AND MANUFACTURING METHOD THEREOF

(71) Applicants: Dadong Zhang, Shanghai (CN); Xu Cai, Shanghai (CN); Chengyun Yue, Shanghai (CN); Junfei Li, Sanghai (CN); Yan Hu, Shanghai (CN); Peng Huang, Shanghai (CN); Zhirong Tang, Shanghai (CN); Qiyi Luo, Shanghai (CN)

(72) Inventors: Dadong Zhang, Shanghai (CN); Xu Cai, Shanghai (CN); Chengyun Yue, Shanghai (CN); Junfei Li, Sanghai (CN); Yan Hu, Shanghai (CN); Peng Huang, Shanghai (CN); Zhirong Tang, Shanghai (CN); Qiyi Luo, Shanghai (CN)

(73) Assignee: SHANGHAI MICROPORT MEDICAL (GROUP) CO., LTD. (CN)

( * ) Notice: Subject to any disclaimer, the term of this patent is extended or adjusted under 35 U.S.C. 154(b) by 0 days.

(21) Appl. No.: 14/677,741

(22) Filed: Apr. 2, 2015

(65) Prior Publication Data
US 2015/0209485 A1    Jul. 30, 2015

Related U.S. Application Data

(63) Continuation of application No. 14/348,857, filed as application No. PCT/CN2012/070400 on Jan. 16, 2012, now abandoned.

(30) Foreign Application Priority Data

Sep. 29, 2011    (CN) .......................... 2011 1 0295324

(51) Int. Cl.
A61L 31/10    (2006.01)
A61L 31/14    (2006.01)
(Continued)

(52) U.S. Cl.
CPC ................... *A61L 31/10* (2013.01); *A61F 2/82* (2013.01); *A61L 31/146* (2013.01); *A61L 31/16* (2013.01);
(Continued)

(58) Field of Classification Search
None
See application file for complete search history.

(56) References Cited

U.S. PATENT DOCUMENTS 6,273,913 B1 * 8/2001 Wright ...................... A61F 2/91
623/1.39
8,003,122 B2    8/2011 Zhao
(Continued)

FOREIGN PATENT DOCUMENTS

CN           1935274 A  *  3/2007
CN       101318032 A     12/2008
(Continued)

OTHER PUBLICATIONS

International Search Report and Written Opinion for PCT/CN2012/070455, dated Apr. 26, 2012, 13 pages.
(Continued)

*Primary Examiner* — Carlos Azpuru
*Assistant Examiner* — Casey Hagopian
(74) *Attorney, Agent, or Firm* — Hovey Williams LLP

(57) ABSTRACT

An interventional medical device and manufacturing method thereof. The interventional medical device comprises: a stent body (1); a surface of the stent body (1) being provided with a drug releasing structure (3), and drug in the drug releasing structure (3) being drug for suppressing proliferation of adventitial fibroblasts and a drug for suppressing proliferation of intimal and/or smooth muscle cells. In use, after interventional medical device is implanted into a human body, the drug for suppressing proliferation of adventitial fibroblasts carried thereon can promote the compensatory expansion of the vessel, and the drug for suppressing proliferation of intimal cells and/or smooth muscle cells carried thereon can suppress intimal proliferation of the vessel. The combination of the two kinds of drugs greatly reduces the occurrence rate of in-stent restenosis.

13 Claims, 4 Drawing Sheets

(51) Int. Cl.
  *A61L 31/16* (2006.01)
  *A61F 2/82* (2013.01)

(52) U.S. Cl.
  CPC ... *A61F 2250/0067* (2013.01); *A61F 2250/0068* (2013.01); *A61L 2300/416* (2013.01); *A61L 2420/02* (2013.01)

(56) References Cited

U.S. PATENT DOCUMENTS

| | | |
|---|---|---|
| 2004/0086542 A1* | 5/2004 | Hossainy ............ A61L 27/34 424/423 |
| 2005/0060028 A1* | 3/2005 | Horres ............ A61L 31/10 623/1.38 |
| 2006/0199876 A1* | 9/2006 | Troczynski ............ A61L 27/32 523/115 |
| 2007/0037883 A1 | 2/2007 | Dusting et al. |
| 2007/0219613 A1 | 9/2007 | Kao et al. |
| 2007/0292470 A1* | 12/2007 | Thornton ............ A61L 31/048 424/423 |
| 2009/0112310 A1* | 4/2009 | Zhang ............ A61L 31/146 623/1.42 |
| 2011/0202122 A1 | 8/2011 | Takeuchi et al. |
| 2011/0202125 A1 | 8/2011 | Luo et al. |

FOREIGN PATENT DOCUMENTS

| | | |
|---|---|---|
| CN | 101879102 A | 11/2010 |
| EP | 2014308 A2 | 1/2009 |
| WO | 2013044605 A1 | 4/2013 |

OTHER PUBLICATIONS

International Search Report and Written Opinion for PCT/CN2012/070400, dated Jul. 5, 2012, 12 pages.

* cited by examiner

INTERVENTIONAL MEDICAL DEVICE AND MANUFACTURING METHOD THEREOF

FIELD OF THE INVENTION

The present application relates to the technical field of medical devices, inparticular, to an interventional medical device containing drugs and manufacturing method thereof.

BACKGROUND ARTS

In recent years, a drug coating was coated onto the stent implanted in the body so as to avoid the incidence of in-stent restenosis after interventional treatment. Drugs mostly carried by currently used drug-eluting stents are those for inhibiting intimal hyperplasia or tunica media hyperplasia, including rapamycin, paclitaxel and derivatives thereof, etc. When the stent carrying above-mentioned drug is implanted into a human body, the stent will continuously release the drug for inhibiting intimal hyperplasia or tunica media hyperplasia into vessel wall to reduce the occurrence rate of in-stent restenosis.

Studies have shown that vascular restenosis formation is not only related to intimal hyperplasia or tunica media hyperplasia after vascular injury, but also related to vascular remodelling. Vascular remodeling is the main factor for in-stent restenosis, accounting for 70% possible causes of restenosis, while intimal hyperplasia or tunica media hyperplasia accounts for only 30% possible causes of restenosis.

Therefore, the current drug-eluting stents for inhibiting intimal hyperplasia or tunica media hyperplasia can not reduce the incidence of in-stent restenosis to the greatest extent. In addition, the current drugs for inhibiting intimal hyperplasia or tunica media hyperplasia, such as rapamycin, paclitaxel and derivatives thereof, may suppress endothelial cell growth, and delay vascular endothelialisation. The problem that blood vessels can not be completely endothelialized may cause late thrombosis.

SUMMARY OF THE INVENTION

In view thereof, the examples of the present application provide an interventional medical device and manufacturing method thereof. The interventional medical device can promote vascular compensatory expansion by suppressing proliferation of adventitial fibroblasts, after it is implanted into a human body. And it may also inhibit intimal hyperplasia to reduce the occurrence rate of in-stent restenosis.

In order to achieve the above objects, the examples of the present application provide the following technical solutions:

An interventional medical device, comprising a stent body with a drug releasing structure on its surface, and the drugs in the drug releasing structure are drugs for suppressing proliferation of adventitial fibroblasts and for suppressing proliferation of intimal cells and/or smooth muscle cells.

Preferably, the drug releasing structure is a dense mixed layer formed by a polymer and the drug for suppressing adventitial fibroblast proliferation and the drug for suppressing proliferation of intimal cells and/or smooth muscle cells.

Preferably, the polymer includes polylactic acid, polyethylene glycol, styrene-butene copolymer, polycaprolactone, poly(butyl methacrylate), poly(ethyl methacrylate), polyvinyl ethyl acetate, polyurethane, polyvinyl pyrrolidone, polyphosphorylcholine, silk protein, gelatin, chitin and/or hyaluronic acid.

Preferably, the drug releasing structure is a microporous structure prepared on the surface of the stent body or a microporous coating structure formed on the surface of the stent body, and the drug is loaded into the microporous structure or the microporous coating structure.

Preferably, the drug for suppressing adventitial fibroblast proliferation include at least one drug selected from the group consisting of tanshinone, asiaticoside, madecassoside, ligustrazine, dracorhodin, Rosuvastatin, and angiotensin.

Preferably, the drug for suppressing proliferation of intimal cells and/or smooth muscle cells include at least one drug selected from the group consisting of rapamycin and derivative thereof, paclitaxel and derivative thereof.

Preferably, the stent body comprises coronary artery stent, intracranial vascular stent, peripheral vascular stent, intraoperative stent, heart valve stent, biliary tract stent, esophageal stent, intestinal tract stent, pancreatic duct stent, urethral stent or tracheal stent.

A method for preparing an interventional medical device, comprising:

preparing a microporous structure on the surface of a stent body;

formulating a solution containing a drug for suppressing proliferation of adventitial fibroblasts and a drug for suppressing proliferation of intimal cells and/or smooth muscle cells;

loading the drugs within the formulated solution into said microporous structure;

drying the stent body to obtain the interventional medical device.

Preferably, preparing a microporous structure on the surface of the stent body comprises forming micropores on the surface of the stent body by anodic oxidation, micro-arc oxidation and/or chemical corrosion.

Preferably, preparing a microporous structure on the surface of the stent body comprises preparing a coating having micropores on the surface of the stent body.

Preferably, loading the drugs within the formulated solution into said microporous structure comprises loading the drugs within said solution into said microporous structure by ultrasonic spraying, air spraying and/or dipping.

A method for preparing an interventional medical device, comprising:

formulating a mixed solution of a drug for suppressing adventitial fibroblast proliferation and a polymer, as well as a mixed solution of a drug for suppressing proliferation of intimal cells and/or smooth muscle cells and a polymer, respectively, or formulating a mixed solution of a drug for suppressing adventitial fibroblast proliferation, a drug for suppressing proliferation of intimal cells and/or smooth muscle cells and a polymer;

successively coating the surface of the stent body with the mixed solution of the drug for suppressing adventitial fibroblast proliferation and the polymer, as well as the mixed solution of the drug for suppressing proliferation of intimal cells and/or smooth muscle cells and the polymer, or coating the surface of the stent body with the mixed solution of the drug for suppressing adventitial fibroblast proliferation and the drug for suppressing proliferation of intimal cells and/or smooth muscle cells and the polymer;

drying the stent body to obtain the interventional medical device.

Preferably, the coating comprises ultrasonic spraying, air spraying and/or dipping.

It can be seen from the above technical solutions that, when the interventional medical device is used, the drug for suppressing adventitial fibroblast proliferation carried thereon can be slowly released into vessel wall cells in contact with the stent body after it is implanted into a human body, thus inhibiting proliferation of adventitial fibroblasts, functioning in vascular remodeling by blocking fibroblast proliferation, promoting the compensatory expansion of the damaged blood vessel, thereby reducing the occurrence rate of in-stent restenosis. Meanwhile, the drug for suppressing proliferation of intimal cells and/or smooth muscle cells can suppress intimal proliferation of the vessel to some extent. Combination of the two kinds of drugs can greatly reduce the occurrence rate of in-stent restenosis.

In addition, compared with the current drug-eluting stents using rapamycin, paclitaxel and derivatives thereof, the interventional medical device provided by the examples of the present application not only has low inhibition rate on endothelial cells, but also promotes endothelial cell growth and accelerates the process of endothelialization.

ILLUSTRATION

In order to more clearly illustrate the technical solutions of the examples of the present application or the prior art, the accompanying drawings which are required to be used in the description of the examples or the prior art will be briefly introduced below. It is apparent that the accompanying drawings in the following description are merely some examples described in the present application. For those of ordinary skill in the art, it is also possible to derive other drawings according to these drawings without creative efforts.

DETAILED DESCRIPTION OF THE INVENTION

In order to make those skilled in the art better understand technical solutions of the present application, the technical solutions of the examples of the present application will be clearly and fully described below by making reference to the accompanying drawings of the examples of the present application. Obviously, the described examples are merely a part of the examples of the present application, but not all examples. Based on the examples of the present application, all other examples obtained by those of ordinary skill in the art without creative efforts, should fall within the protection scope of the present application.

The examples of the present application provide an interventional medical device, comprising a stent body with a drug releasing structure, wherein the drugs in the drug releasing structure are drugs for suppressing proliferation of adventitial fibroblasts and for suppressing proliferation of intimal cells and/or smooth muscle cells.

An Example

Figure 1:
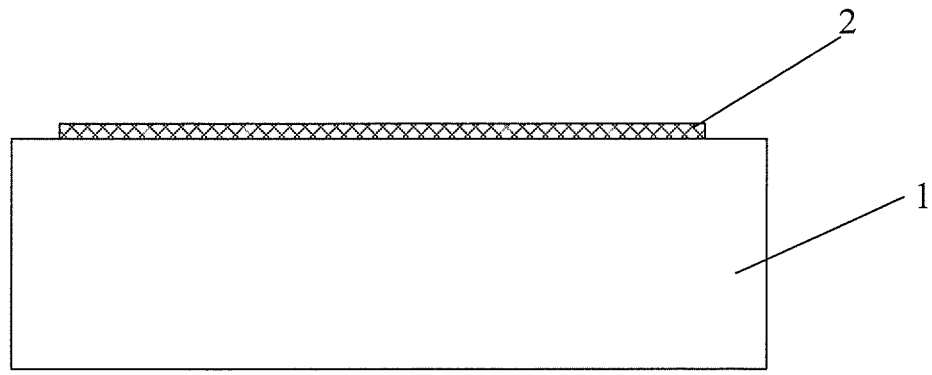
FIG. 1 is a structural schematic diagram of a specific embodiment of the interventional medical device provided by the present application.

FIG. 1 is a structural schematic diagram of a specific embodiment of the interventional medical device provided by the present application.

As shown in FIG. 1, 1 indicates stent body, 2 indicates drug releasing coating. Drug releasing coating 2 is coated on the outer surface of stent body 1, in which:

Stent body 1 can be a coronary artery stent, intracranial vascular stent, peripheral vascular stent, intraoperative stent, heart valve stent, biliary tract stent, esophageal stent, intestinal tract stent, pancreatic duct stent, urethral stent or tracheal stent. Furthermore, the material of stent body 1 can be a material with good biocompatibility and mechanical characteristics, such as stainless steel, cobalt-based alloy, nickel-based alloy, titanium alloy, degradable magnesium alloy or a polymer material, etc.

Drug releasing coating 2 is a dense mixed layer formed by the polymer and the drug for suppressing adventitial fibroblast proliferation and the drug for suppressing proliferation of intimal cells and/or smooth muscle cells. That is, drug releasing coating 2 is used as a carrier to allow the surface of stent body 1 to carry drugs.

Drug for inhibiting adventitial fibroblast proliferation includes at least one drug selected from the group consisting of tanshinone, asiaticoside, madecassoside, ligustrazine, dracorhodin, Rosuvastatin, angiotensin. In the examples of the present application, asiaticoside is preferred. Drug for suppressing proliferation of intimal cells and/or smooth muscle cells can be at least one drug selected from the group consisting of rapamycin and derivative thereof and paclitaxel and derivative thereof, with rapamycin is preferred. In addition, the polymer in drug releasing coating 2 can be a polymer having biocompatibility and controlled release properties, such as, polylactic acid, polyethylene glycol, styrene-butene copolymer, polycaprolactone, poly(butyl methacrylate), poly(ethyl methacrylate), polyvinyl ethyl acetate, polyurethane, polyvinyl pyrrolidone, polyphosphorylcholine, silk protein, gelatin, chitin and/or hyaluronic acid.

Asiaticoside is the total glycosides extracted from Umbelliferae *Centella asiatica*. Asiaticoside can inhibit the pathological role of TGF-beta by increasing expression of Smad7 that inhibits Smad transduction signal, thereby functioning in vascular remodeling by blocking fibroblast proliferation, promoting vascular compensatory expansion, thus reducing the occurrence rate of in-stent restenosis.

Furthermore, studies have found that asiaticoside could also promote endothelial cell growth and accelerate endothelialization process. For detailed, see "Experimental study of the effect of asiaticoside on preventing restenosis after percutaneous coronary intervention (CLC R541.4 Article ID: 1671-8259 (2005) 05-0477-03).

Thus it can be seen that, compared with the current drug-eluting stents using rapamycin, paclitaxel and derivatives thereof, the interventional medical device provided by the examples of the present application also promotes endothelial cell growth and accelerates the process of endothelialization.

Another Example

Figure 2:
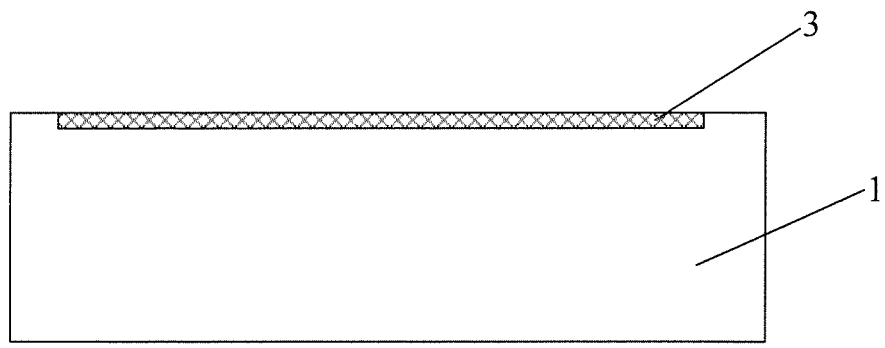
FIG. 2 is a structural schematic diagram of another specific embodiment of the interventional medical device provided by the present application.

FIG. 2 is a structural schematic diagram of another specific embodiment of the interventional medical device provided by the present application.

As shown in FIG. 2, 1 indicates stent body, 3 indicates micropores formed on the surface of the stent. In the example of the present application, the drug releasing structure is micropore 3. Micropore 3 may be obtained by oxidating or eroding the surface of stent body 1. Drugs may be loaded within micropore 3, thus, the surface of stent body 1 will carry drugs.

A Further Example

Figure 3:
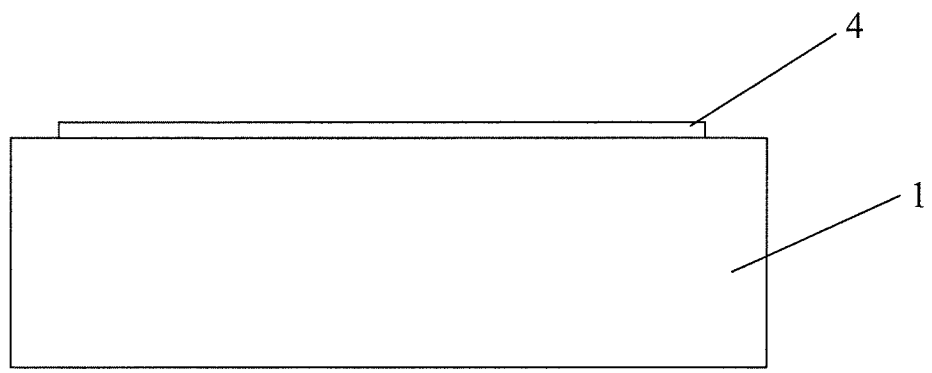
FIG. 3 is a structural schematic diagram of another specific embodiment of the interventional medical device provided by the present application.

FIG. 3 is structural schematic diagram of another specific embodiment of the interventional medical device provided by the present application.

In the interventional medical device shown in FIG. 2, micropore 3 is obtained by directly oxidating or eroding the surface of stent body 1. However, in the example of the present application, a layer of microporous coating can be prepared on the surface of stent body 1. As shown in FIG. 3, 1 indicates stent body, 4 indicates microporous coating. This eliminates the need for oxidating or eroding the surface of stent body 1. On the contrary, microporous coating 4 is directly prepared on the surface of stent body 1 to obtain micropores loaded with drugs.

A Further Example

Figure 4:
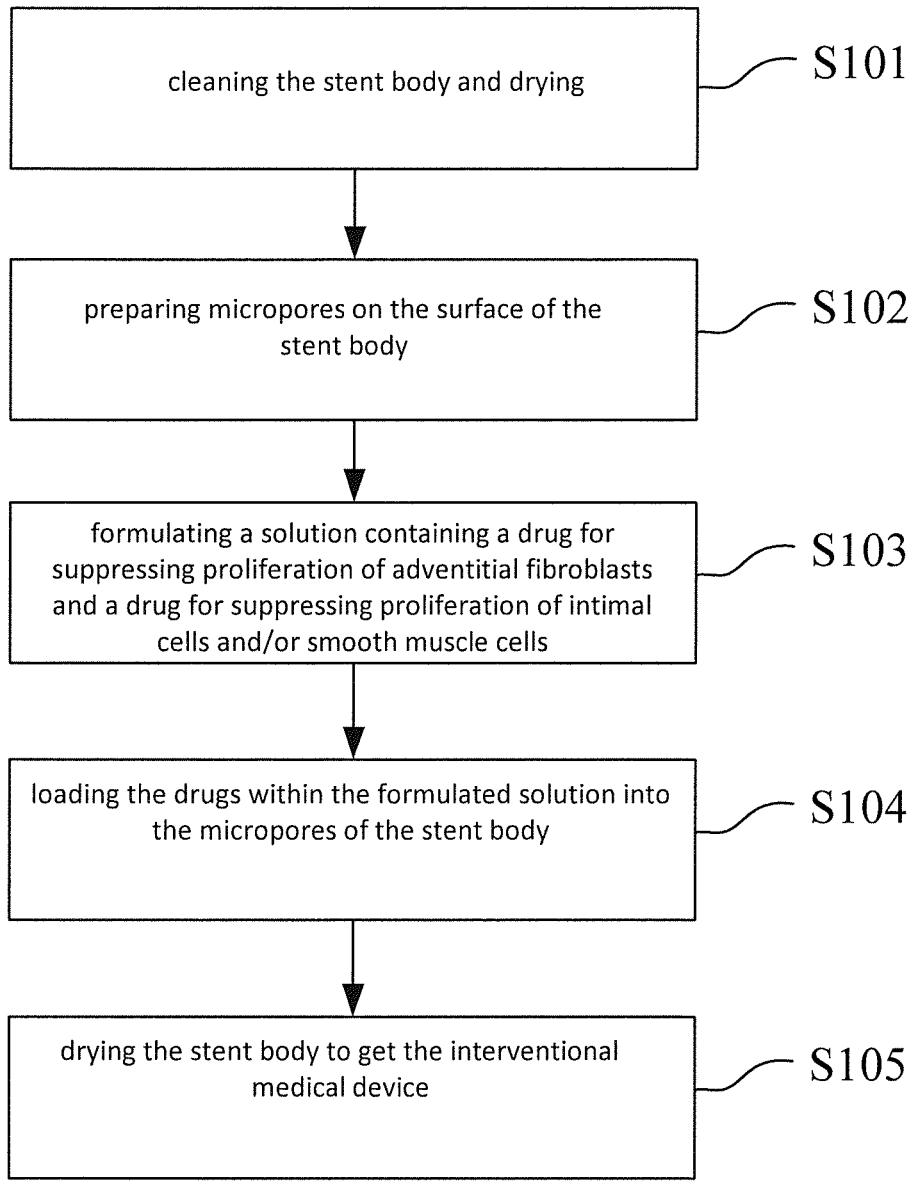
FIG. 4 is a technological process of the preparation method of the interventional medical device provided by the present application.

FIG. 4 is a technological process of the preparation method of the interventional medical device provided by the present application.

As shown in FIG. 4, in the example of the present application, taking metal stent as an example of the stent body, the preparation method of the interventional medical device comprises:

Step S101: cleaning the stent body and drying.

During the preparation of the interventional medical device, in order to prevent residual stains on the stent body from affecting the quality of the interventional medical device, it is necessary to clean the stent body first.

Step S102: preparing micropores on the surface of the stent body.

Micropores on the surface of the stent body are formed by electrochemical corrosion and/or chemical corrosion. Electrochemical corrosion includes anodic oxidation, micro-arc oxidation and so on. Micropores can be formed on the surface of the stent body by this step. FIG. 2 shows their structural schematic diagram.

Step S103: formulating a solution containing a drug for suppressing proliferation of adventitial fibroblasts and a drug for suppressing proliferation of intimal cells and/or smooth muscle cells.

In the example of the present application, preferably, the drug for suppressing proliferation of adventitial fibroblasts is asiaticoside, and the drug for suppressing proliferation of intimal cells and/or smooth muscle cells is rapamycin. A mixed solution of asiaticoside and rapamycin is formulated, in which asiaticoside:rapamycin=2:1~5:1. When formulating, 10 mg rapamycin and 30 mg asiaticoside are dissolved in 10 ml ethanol solution. After they are dissolved, the mixture is mixed thoroughly.

Step S104: loading the drugs within the formulated solution into the micropores of the stent body.

The stent body with micropores on its surface obtained in step S102 is immersed into the solution formulated in step S103, so that the drugs within the solution can be loaded into the micropores on the surface of the stent body.

Step S105: drying the stent body to get the interventional medical device.

A Further Example

Figure 5:
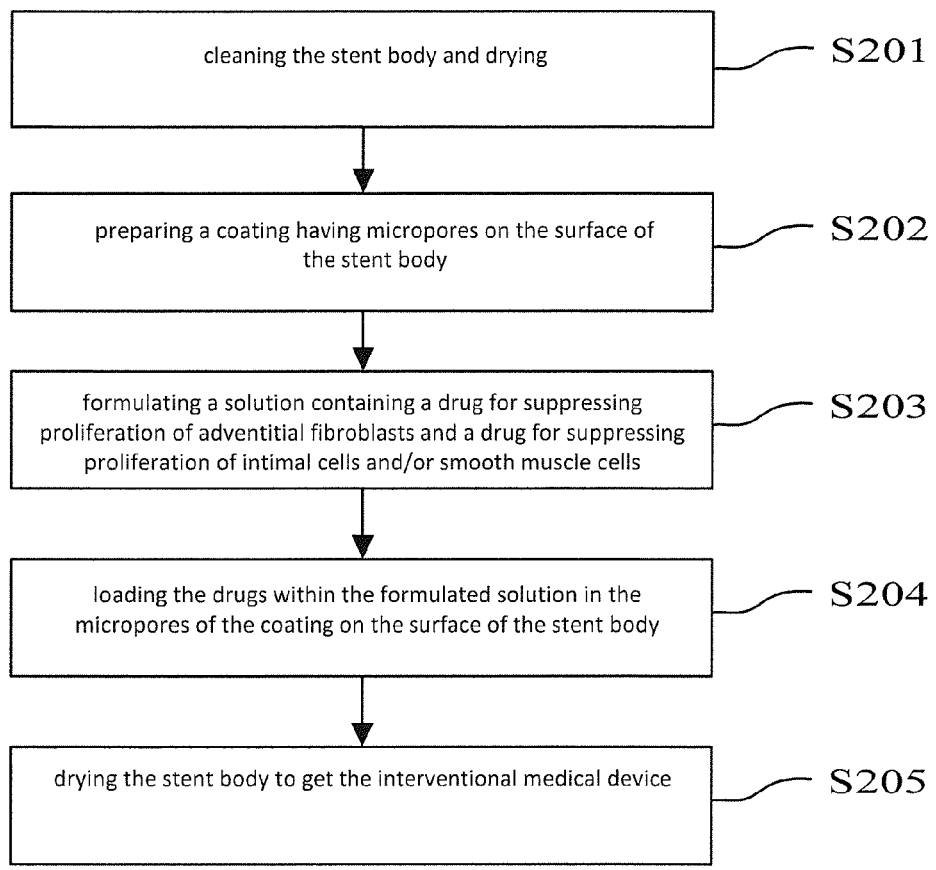
FIG. 5 is another technological process of the preparation method of the interventional medical device provided by the present application.

FIG. 5 is another technological process of the preparation method of the interventional medical device provided by the present application.

As shown in FIG. 5, in the example of the present application, the preparation method of the interventional medical device comprises:

Step S201: cleaning the stent body and drying.

Step S202: preparing a coating having micropores on the surface of the stent body.

Particular process includes the following steps: the silk protein solution is uniformly coated on the surface of the stent body. Then the stent body is subject to thermal or chemical denaturation, and infiltration by pure water. After that, the stent body is freezed and then the temperature is increased to dry the stent body. A coating with microporous structure is thus formed on the surface of the stent body.

Step S203: formulating a solution containing a drug for suppressing proliferation of adventitial fibroblasts and a drug for suppressing proliferation of intimal cells and/or smooth muscle cells.

In the example of the present application, preferably, the drug for suppressing proliferation of adventitial fibroblasts is asiaticoside, and the drug for suppressing proliferation of intimal cells and/or smooth muscle cells is rapamycin. When formulating, 10 mg rapamycin and 50 mg asiaticoside are dissolved in 10 ml ethanol solution. After they are dissolved, the mixture is mixed thoroughly.

Step S204: loading the drugs within the formulated solution into the micropores of the coating on the surface of the stent body.

The stent body with a microporous coating on its surface obtained in step S202 is immersed into the formulated solution, so that the drugs within the solution can be loaded into the micropores of the coating on the surface of the stent body.

Step S205: drying the stent body to get the interventional medical device.

A Further Example

Figure 6:
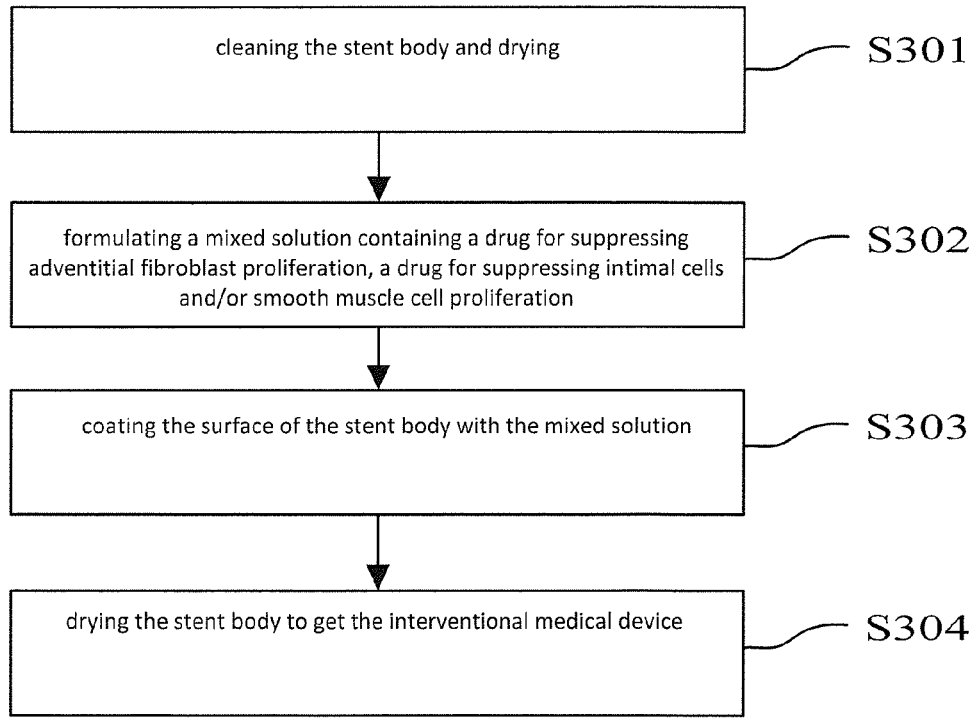
FIG. 6 is another technological process of the preparation method of the interventional medical device provided by the present application.

FIG. 6 is another technological process of the preparation method of the interventional medical device provided by the present application.

As shown in FIG. 6, in the example of the present application, the preparation method of the interventional medical device comprises:

Step S301: cleaning the stent body and drying.

Step S302: formulating a mixed solution containing a drug for suppressing adventitial fibroblast proliferation, a drug for suppressing intimal cells and/or smooth muscle cell proliferation and a polymer.

In the example of the present application, the polymer is polylactic acid, the drug for suppressing proliferation of adventitial fibroblasts is preferably asiaticoside, and the drug for suppressing proliferation of intimal cells and/or smooth muscle cells is preferably rapamycin. A mixed solution of polylactic acid, asiaticoside and rapamycin is formulated, in which the ratio of asiaticoside and rapamycin is in the range of 2:1~5:1, and the ratio of polylactic acid and asiaticoside is in the range of 1:1~5:1. When formulating, 10 mg rapamycin, 30 mg asiaticoside and 10 mg polylactic acid can be added to 10 ml tetrahydrofuran. After they are sufficiently dissolved, the mixture is mixed uniformly.

Step S303: coating the surface of the stent body with the mixed solution.

In the example of the present application, the mixed solution formulated in step 302 can be coated on the stent body by ultrasonic spraying, air spraying or dipping.

Step S304: drying the stent body to get the interventional medical device.

A Further Example

In FIG. 6, a mixed solution of two drugs and the polymer is formulated. However, in the practical application, two drugs can be mixed with the polymer respectively. Then the mixed solutions of each drug are successively coated on the surface of the stent body.

Figure 7:
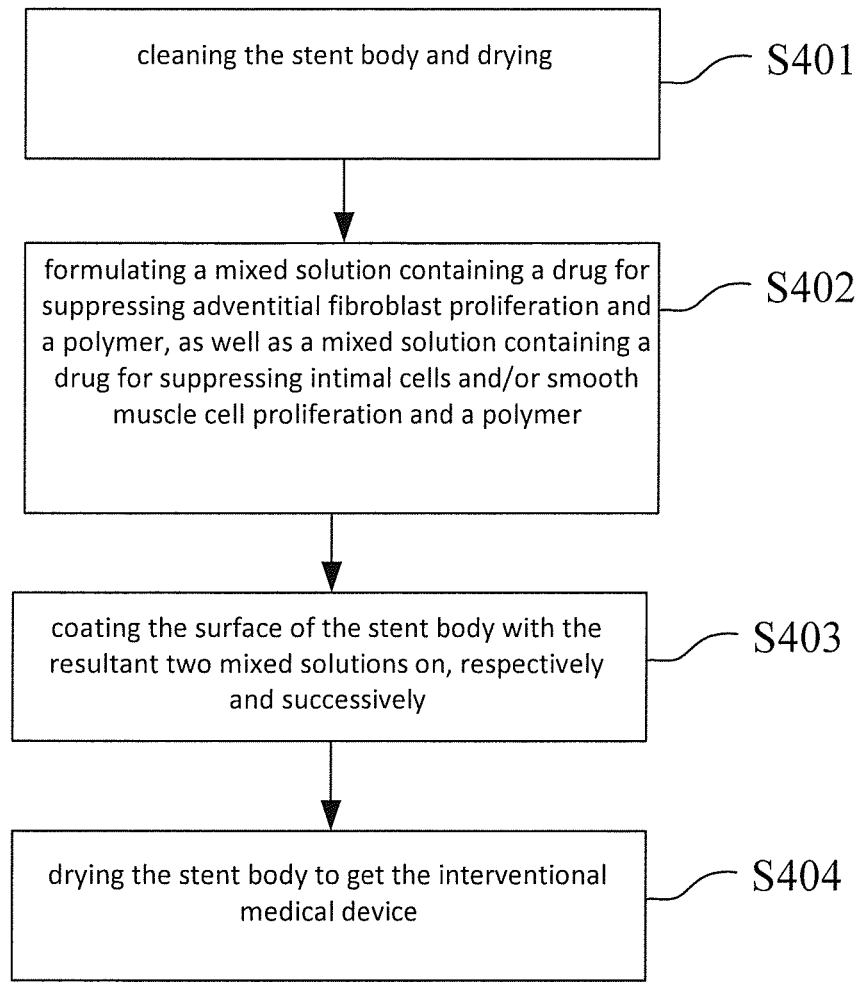
FIG. 7 is another technological process of the preparation method of the interventional medical device provided by the present application.

FIG. 7 is another technological process of the preparation method of the interventional medical device provided by the present application.

As shown in FIG. 7, in the example of the present application, the preparation method of the interventional medical device comprises:

Step S401: cleaning the stent body and drying.

Step S402: formulating a mixed solution containing a drug for suppressing adventitial fibroblast proliferation and a polymer, as well as a mixed solution containing a drug for suppressing intimal cells and/or smooth muscle cell proliferation and a polymer.

In the example of the present application, preferably, the polymer is polylactic acid, the drug for suppressing proliferation of adventitial fibroblasts is asiaticoside, and the drug for suppressing proliferation of intimal cells and/or smooth muscle cells is rapamycin. Solution of polylactic acid and asiaticoside and solution of polylactic acid and rapamycin are formulated respectively, in which, the ratio of polylactic acid and asiaticoside is in the range of 1:1~4:1, and the ratio of polylactic acid and rapamycin is in the range of 1:1~4:1. When formulating, 30 mg asiaticoside and 60 mg polylactic acid are added to 10 ml tetrahydrofuran. After they are sufficiently dissolved, the mixture is mixed uniformly to get a first drug solution. Additionally, 10 mg rapamycin and 20 mg polylactic acid are added to 10 ml tetrahydrofuran. After they are sufficiently dissolved, the mixture is mixed uniformly to get a second drug solution.

Step S403: coating the surface of the stent body with the resultant two mixed solutions on, respectively and successively.

When coating, asiaticoside/polylactic acid solution can be coated on the surface of the stent body first. Then the sprayed stent body is placed in the air for 4 h to make its surface dried. After that, rapamycin/polylactic acid solution is coated on the surface of the dried stent body.

During above-mentioned spray coating, asiaticoside/polylactic acid solution is sprayed first, followed by rapamycin/polylactic acid solution. This is only an example of the present application, and should not be construed to limit the present application. Those of ordinary skill in the art should know that, in other examples, the spraying order of the two drug solutions can be freely chosen.

In addition, in the example of the present application, ultrasonic spraying, air spraying or dipping and other means may be used.

Step S404: drying the stent body to get the interventional medical device.

The above examples are only preferred embodiments of the present application. With these examples the skilled person can understand or realize the present application. Various modifications to these examples will be apparent to the skilled person in the art, and the generic principles defined herein may be implemented in other examples without departing from the spirit or scope of the present application. Accordingly, the present application will not be limited to these examples described herein, but meet the widest scope consistent with the principles and novel features disclosed herein.

What is claimed is:

1. An interventional medical device, comprising a stent body with a drug releasing structure on its surface and at least one drug for suppressing proliferation of adventitial fibroblast fibroblasts and at least one drug for suppressing proliferation of intimal cells and/or smooth muscle cells loaded on or in said drug releasing structure, wherein said at least one drug for suppressing adventitial fibroblast proliferation is or includes asiaticoside and said at least one drug for suppressing proliferation of intimal cells and/or smooth muscle cells is or includes rapamycin, wherein the ratio between the weight of asiaticoside and that of rapamycin present in the drug releasing structure is from 2:1 to 5:1.

2. The interventional medical device according to claim 1, wherein said drug releasing structure is a dense mixed layer formed by a polymer and the drug for suppressing adventitial fibroblast proliferation and the drug for suppressing proliferation of intimal cells and/or smooth muscle cells.

3. The interventional medical device according to claim 2, wherein said polymer includes polylactic acid, polyethylene glycol, styrene-butene copolymer, polycaprolactone, poly (butyl methacrylate), poly (ethyl methacrylate), polyvinyl ethyl acetate, polyurethane, polyvinyl pyrrolidone, polyphosphorylcholine, silk protein, gelatin, chitin and/or hyaluronic acid.

4. The interventional medical device according to claim 1, wherein, said drug releasing structure is a microporous structure prepared on the surface of said stent body or a microporous coating structure formed on the surface of said stent body, and the drugs are loaded into said microporous structure or microporous coating structure.

5. The interventional medical device according to claim 1, wherein said at least one drug for suppressing adventitial fibroblast proliferation additionally includes at least one drug selected from the group consisting of tanshinone, madecassoside, ligustrazine, dracorhodin, rosuvastatin, and angiotensin.

6. The interventional medical device according to claim 1, wherein said at least one drug for suppressing proliferation of intimal cells and/or smooth muscle cells additionally includes at least one drug selected from the group consisting of derivatives of rapamycin and paclitaxel and derivative thereof.

7. The interventional medical device according to claim 1, wherein said stent body comprises a coronary artery stent, an intracranial vascular stent, a peripheral vascular stent, an intraoperative stent, a heart valve stent, a biliary tract stent, an esophageal stent, an intestinal tract stent, a pancreatic duct stent, an urethral stent or a tracheal stent.

8. A method for preparing an interventional medical device, wherein said method comprises:
preparing a microporous structure on the surface of the stent body;

formulating a solution containing at least one drug for suppressing proliferation of adventitial fibroblasts and at least one drug for suppressing proliferation of intimal cells and/or smooth muscle cells, wherein said at least one drug for suppressing adventitial fibroblast proliferation is or includes asiaticoside and said at least one drug for suppressing proliferation of intimal cells and/or smooth muscle cells is or includes rapamycin, loading the drugs within the formulated solution into said microporous structure, wherein the ratio between the weight of asiaticoside and that of rapamycin present in the microporous structure is from 2:1 to 5:1;

drying the stent body to obtain said interventional medical device.

9. The method according to claim 8, wherein, preparing a microporous structure on the surface of the stent body comprises forming micropores on the surface of the stent body by anodic oxidation, micro-arc oxidation and/or chemical corrosion.

10. The method according to claim 8, wherein preparing a microporous structure on the surface of the stent body comprises preparing a coating having micropores on the surface of said stent body.

11. The method according to claim 8, wherein loading the drugs within the formulated solution into said microporous structure comprises loading the drugs within said solution into said microporous structure by ultrasonic spraying, air spraying and/or dipping.

12. A method for preparing an interventional medical device, wherein said method comprises:

formulating a mixed solution of a drug for suppressing adventitial fibroblast proliferation and a polymer, as well as a mixed solution of a drug for suppressing proliferation of intimal cells and/or smooth muscle cells and a polymer, respectively, or formulating a mixed solution of a drug for suppressing adventitial fibroblast proliferation, a drug for suppressing proliferation of intimal cells and/or smooth muscle cells and a polymer, wherein said drug for suppressing adventitial fibroblast proliferation is asiaticoside and said drug for suppressing proliferation of intimal cells and/or smooth muscle cells is rapamycin;

successively coating the surface of the stent body with the mixed solution of the drug for suppressing adventitial fibroblast proliferation and the polymer, as well as the mixed solution of the drug for suppressing proliferation of intimal cells and/or smooth muscle cells and the polymer, or coating the surface of the stent body with the mixed solution of the drug for suppressing adventitial fibroblast proliferation, the drug for suppressing proliferation of intimal cells and/or smooth muscle cells and the polymer;

drying the stent body to obtain the interventional medical device, wherein the ratio between the weight of asiaticoside and that of rapamycin present in the interventional medical device is from 2:1 to 5:1.

13. The method according to claim 12, wherein said coating comprises ultrasonic spraying, air spraying and/or dipping.

* * * * *